(12) United States Patent
Levens et al.

(10) Patent No.: US 8,708,701 B2
(45) Date of Patent: Apr. 29, 2014

(54) VIBRATING DENTAL PLATE AND ACCESSORIES

(75) Inventors: Lawrence Levens, Houston, TX (US); W. Brent Tarver, Houston, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 0 days.

(21) Appl. No.: 13/057,964

(22) PCT Filed: Feb. 9, 2010

(86) PCT No.: PCT/US2010/023635
§ 371 (c)(1),
(2), (4) Date: Oct. 5, 2011

(87) PCT Pub. No.: WO2010/093632
PCT Pub. Date: Aug. 19, 2010

(65) Prior Publication Data
US 2012/0040300 A1 Feb. 16, 2012

Related U.S. Application Data

(60) Provisional application No. 61/151,249, filed on Feb. 10, 2009.

(51) Int. Cl.
*A61B 5/117* (2006.01)
(52) U.S. Cl.
USPC .............................. 433/229; 433/3; 433/214
(58) Field of Classification Search
CPC ........ A61C 17/22; A61C 17/221; A61C 9/00; A61C 9/0006
USPC ............ 433/48, 80, 37, 136, 214, 215, 3, 229
See application file for complete search history.

(56) References Cited

U.S. PATENT DOCUMENTS

| | | | |
|---|---|---|---|
| 3,482,312 | A | 12/1969 | Smith |
| 3,802,302 | A | 4/1974 | Bengtson |
| 4,244,688 | A | 1/1981 | Kurz |
| 4,348,177 | A | 9/1982 | Kurz |
| 4,382,780 | A | 5/1983 | Kurz |

(Continued)

FOREIGN PATENT DOCUMENTS

| | | |
|---|---|---|
| JP | 2007260158 A | 10/2007 |
| WO | WO2007/146703 | 12/2007 |
| WO | 2009158297 | 12/2009 |
| WO | WO2010/093632 | 8/2010 |

OTHER PUBLICATIONS

Aqualizer Dental Splints for TMJ Pain Relief and Treatment, http://www.aqualizer.com/, May 11, 2010.

(Continued)

*Primary Examiner* — Eric Rosen
(74) *Attorney, Agent, or Firm* — Boulware & Valoir

(57) ABSTRACT

Vibrating dental devices and accessories are provided, including a unique snap fit dental plate and vibrator connection; risers for adjusting the thickness of a dental plate; a pointer or wand that can be clamped onto a dental plate to reach even severely misaligned teeth; a cushioned dental plate having a non-Newtonian fluid therein that allows conformation of the cushion to the dentition, but hardens on use to allow the transmission of vibration to the teeth. Accessories such as carrying cases and docking stations are also provided.

3 Claims, 8 Drawing Sheets

(56) References Cited

U.S. PATENT DOCUMENTS

| | | | |
|---|---|---|---|
| 4,531,916 A | | 7/1985 | Scantlebury et al. |
| 4,690,776 A | * | 9/1987 | Smigel .......................... 424/49 |
| 4,763,791 A | | 8/1988 | Halverson et al. |
| 4,883,046 A | | 11/1989 | Fontenot |
| 4,955,393 A | * | 9/1990 | Adell .......................... 128/859 |
| 5,030,098 A | * | 7/1991 | Branford ...................... 433/215 |
| 5,100,567 A | * | 3/1992 | Naae et al. ................... 507/216 |
| 5,234,005 A | * | 8/1993 | Kittelsen et al. ............. 128/859 |
| 5,336,092 A | | 8/1994 | Chalifoux |
| 5,645,878 A | | 7/1997 | Breslin et al. |
| 5,967,784 A | | 10/1999 | Powers |
| 6,083,002 A | * | 7/2000 | Martin et al. .................. 433/90 |
| 6,632,088 B2 | | 10/2003 | Voudouris |
| 6,648,639 B2 | | 11/2003 | Mao |
| 6,832,912 B2 | | 12/2004 | Mao |
| 6,852,774 B1 | | 2/2005 | Engelbrecht |
| 7,029,276 B2 | | 4/2006 | Mao |
| 7,163,399 B2 | | 1/2007 | Kajimoto et al. |
| 7,192,281 B2 | | 3/2007 | Mailyan |
| 7,288,075 B2 | * | 10/2007 | Parihar et al. ................. 600/590 |
| 7,402,147 B1 | * | 7/2008 | Allen ............................. 602/20 |
| 2006/0287620 A1 | | 12/2006 | Tseng |
| 2007/0037116 A1 | * | 2/2007 | Knutson ......................... 433/68 |
| 2007/0161461 A1 | | 7/2007 | Nguyen |
| 2007/0161931 A1 | | 7/2007 | Kunita et al. |
| 2007/0179414 A1 | | 8/2007 | Imboden et al. |
| 2007/0208284 A1 | | 9/2007 | Huang |
| 2007/0255188 A1 | | 11/2007 | Tseng |
| 2007/0259313 A1 | * | 11/2007 | Dragan et al. ................ 433/136 |
| 2007/0299372 A1 | | 12/2007 | Chang |
| 2008/0227046 A1 | | 9/2008 | Lowe et al. |
| 2008/0227047 A1 | | 9/2008 | Lowe et al. |
| 2008/0293007 A1 | * | 11/2008 | Li et al. .......................... 433/80 |
| 2010/0178252 A1 | * | 7/2010 | Sagel et al. .................... 424/9.6 |

OTHER PUBLICATIONS

U.S. Appl. No. 61/040,777, "Vibrating Compressible Dental Plate for Correcting Malocclusion", May 31, 2003.

* cited by examiner

VIBRATING DENTAL PLATE AND ACCESSORIES

PRIOR RELATED APPLICATIONS

This application is a 35 U.S.C. Section 371 of PCT/US10/23635, filed Feb. 9, 2010, which claims priority to U.S. Ser. No. 61/151,249, filed Feb. 10, 2009 and both are incorporated by reference herein.

FEDERALLY SPONSORED RESEARCH STATEMENT

Not applicable.

REFERENCE TO MICROFICHE APPENDIX

Not applicable.

FIELD OF THE INVENTION

The invention relates to vibrating dental devices for correcting malocclusion, and various accessories relating to same.

BACKGROUND OF THE INVENTION

Orthodontics is a dental specialty that treats malocclusion through the movement of teeth as well as control and modification of facial growth. This process is usually accomplished by using a continuous mechanical force to induce bone remodeling, thereby enabling the teeth to move to a better position. In this approach, orthodontic appliances provide a continuous static force to the teeth via an archwire connected to brackets affixed to each tooth or via a removable appliance such as an aligner, or some similar accessory, that fits over the dentition. As the teeth slowly move due to the force, the force is dissipated. The archwires are adjusted to add additional force and to continue the desired tooth movement. Although effective, this widely accepted approach takes about twenty four months on average to achieve success.

Dental researchers have long postulated that a pulsating force might also be used to move teeth more rapidly and to ease the discomfort of traditional orthodontics.

For example, U.S. Pat. No. 4,244,688, U.S. Pat. No. 4,348,177, and U.S. Pat. No. 4,382,780 describe devices used to vibrate the teeth during orthodontic treatment, although each uses a different means of applying a vibration. The U.S. Pat. No. 4,244,688 employs a cumbersome external power source to power one to four small motors, whereas U.S. Pat. No. 4,348,177 uses pulsating fluids moved with the chewing motion of the jaw, and U.S. Pat. No. 4,382,780 uses a radio and speaker to set up a vibration. These devices are mounted on a bulky headgear that surrounds the head and are connected directly to the teeth by its intraoral portions. The devices are cumbersome, difficult to construct, expensive and are very difficult to use, thus reducing patient compliance.

U.S. Pat. No. 5,030,098 by Branford describes a hand-held device that simulates chewing in order to treat periodontal disease by increasing blood flow to the gums. The mouthpiece has a perforated malleable plate such that biting of the mouthpiece results in the plate adapting to the user's bite which, of course, varies with each user. The external vibrator imparts motion to the mouthpiece and thus the user's teeth. The device, however, uses an external power source. Further, the dental plate is brass, and is very unpleasant to bite on, thus necessitating a second exterior coating and further complicating manufacture and cost. Although this device allows some small degree of masticating movement by the user, the degree of motion is actually very small. Further, since the device is not designed for orthodontic use, there is no motivation to modify the device to allow a greater degree of movement.

U.S. Pat. No. 5,967,784 by Powers describes a similar device to that described by Brandford. It too is a hand-held tooth vibrator that is simple and has an exterior motor housing connected to a vibrating interdental mouthpiece portion for gripping between the teeth of the patient. The exterior housing contains a battery and a switch for selectively operating a motor with an off-center weight attached to the motor rotating shaft for creating a high frequency vibration that vibrates the entire device. The mouthpiece is disposable, making the system affordable and more convenient to use. The patent teaches using the device to alleviate pain by inserting the interdental mouthpiece between the teeth and clenching and releasing the teeth over the mouthpiece, in an attempt to engage as many teeth as possible in the transmitted vibrations. The vibration is believed to alleviate discomfort by increasing blood flow.

The devices of Branford and Powers are superficially similar to those of the invention herein, but there are significant differences. Most importantly, there is no recognition in either patent that the vibratory device can be used for alveolar bone remodeling or more rapid tooth movement. Thus, the shape of the dental plate in each case is a very flat U- or Y-shaped member that is largely ineffective for remodeling dentoalveolar bone. Additionally, the vibration is not optimized in frequency and amplitude for remodeling. Finally, neither device is programmable, nor can teeth be differentially vibrated, thus the dentist cannot optimize its usage for each patient, nor monitor patient compliance. All of these shortcomings reduce the effectiveness of these devices for craniofacial bone tissue remodeling uses.

U.S. Pat. No. 6,632,088 describes a bracket with powered actuator mounted thereto to provide vibration, but this device appears to be held completely internal to the patient's mouth, thus again being cumbersome, and thus may affect patient comfort and ultimately patient acceptance of the device.

Mao was probably the first to show that the use of cyclic forces could improve dental straightening in rabbits (see U.S. Pat. No. 6,684,639, U.S. Pat. No. 6,832,912, U.S. Pat. No. 7,029,276). Certain dynamic loading patterns (cycling force with rest periods) were shown to greatly increase bone formation compared to basic dynamic loading. Inserting rest periods is now known to be especially efficacious as it allows mechanosensitivity to be restored to the bone tissue. A point of diminishing returns is reached within each loading session. Therefore, intermittently loading cyclic force can increase the rate of bone formation significantly.

However, the device provided by Mao for use in laboratory animals uses arch wires and brackets with a centrally mounted motor that is held inside the mouth. Therefore, the device would be uncomfortable for the patient to use and there is always some risk of electric shock.

Kajimoto, U.S. Pat. No. 7,163,399, describes a device capable of differential vibration. It is an ultrasonic therapy device with an oscillator embedded in the body and holding members which hold the body next to the affected area. The bodies are fixed in the oral cavity next to an implant to accelerate osteogenesis around implant fixtures by supplying an ultrasonic signal from an external driver to the oscillator. This device is only used with an implant, and does not appear suitable for general orthodontic use.

Mailyan, U.S. Pat. No. 7,192,281, also describes a vibrational system for encouraging osteogenesis. Mailyan inserts plates at growth zones for palatal and jaw defect repair. The plates are vibrated to stimulate neogenesis of bone tissue, and then resized to allow further growth. The process uses the mechanical forces of the jaw to apply pressure to missing palatal bone or a honey jaw defect.

JP2007260158 describes a device capable of differential vibration by virtue of holes in the bite plate. Thus, no vibration is transmitted to those teeth in the holes. Each device however, must be custom made for the patient in order to have the correct fit and hole placement and would require continuous revisions to work in orthodontic treatments.

US20080227047 and US20080227046 by Applicants presents a device that accelerates bone remodeling via non-static loading and includes an extraoral vibratory source and a removable and replaceable intraoral bite plate. However, this device can be further optimized and improved by accessories and/or improved design, materials and engineering, and the inventions described herein provide those improvements.

SUMMARY OF THE INVENTION

It is understood that orthodontic tooth movement requires an application of force to the teeth to stimulate dentoalveolar boney remodeling in the areas surrounding each tooth's root. Without such a force, the necessary cellular response required for tooth movement will not be summoned to the area and tooth movement cannot occur. The speed of the required boney remodeling can therefore become a rate-limiting characteristic for the speed of movement of any particular tooth. Therefore, if the same magnitude of force is not applied to each individual tooth within a single dentition, the speed of tooth movement and perfection of the orthodontic treatment will be slowed as an undesirable consequence. Application of such an equal force requires that the orthodontic appliance(s) applied be customized enough to allow such an individualized application of force to each and every tooth.

This invention continues the work described in applications US20080227047, US20080227046, 61/040,777 and 61/074,884, each incorporated herein by reference, but presents several improvements thereon, as follows:

The first improvement relates to a unique connector between the extraoral vibration motor and the removable bite plate. A unique and patentable connector system will allow the device to be marketed on a razor and blades business model—thus, the vibrator can be sold at cost and have substantial product life through refurbishment, but disposable bite plates may continue to generate income since they are intended for single patient use. Generally, the U-shaped bite plate has a prong that extends from the bite plate outwards and ends in a shape that snap fits into a matched socket on the vibrator. Preferably, the oral end of the prong is of small diameter or thickness to minimize patient discomfort and drooling, but the vibrator end of the prong can be of any shape suitable for a snap fit. In a preferred embodiment, the shape is rectangular, with an optional rectangular recess therein, and a protrusion thereon matches with recessions (or vice versa) in the socket.

In some embodiments, the prong bifurcates into two flexible prongs (like a tuning fork), that fit into a matched socket in the vibrator. On insertion, the prongs are forced slightly together by protrusions on the exterior faces of the forked prongs, allowing the connector to easily slide into the socket until the protrusions engage the matched recession on the vibrator, thus providing a snap fit. Alternatively, the protrusions themselves can be spring based as is common in various devices. For release, the protrusions can be depressed to allow disengagement. This can either be done with a button on the vibrator housing, or if the protrusions show outside the housing of the vibrator, they can be directly pressed by the user. Of course, the reverse placement of protrusions and recessions is also possible. In other embodiments, the prong can insert into said socket and a locking fit be established by turning the dental plate 90 degrees to allow the protrusions to fit into the recessions.

Several improvements described herein address the serious issue of targeting and providing the necessary vibratory forces to those teeth that are insufficiently aligned so as to contact a bite plate that is flat. Several options are described, including the addition of small button-like "risers" to the dental plate so as to reach recessed teeth. Where the riser is attached by screw or snap fit, the bite plate will obviously have corresponding spaced receptors (recessions or holes) for receiving the riser connector, although these can be placed under a polymeric cover, which is then penetrated on the use of a riser with a pin attachment means. If no riser is used, the plate continues to have a smooth blemish free surface.

In another embodiment, risers are available in different heights or thicknesses so as to reach various teeth, and are attached to the bite plate to increase the thickness of the plate locally so as to contact recessed teeth or teeth that are otherwise out of physical contact with said bite plate. In another embodiment a standard riser using a pin or screw like attachment means is combined with small annular adaptors, like washers, and additional washers are used to increase the height of the riser.

The risers can be any suitable shape including a partial sphere, flat or rounded discs, hexagons, squares or rectangles. The use of a riser having a polygonal cross section may be preferred because this will allow closer spacing of risers, and/or the use of socket wrenches in their application. The risers can be made of the same material as the coating on the bite plate and attached by adhesive, heat weld, or other bonding means or a physical attachment means such as a screw, bolt, rivet, pin, snap fit post, or the like. If desired, the riser can also comprise a central rigid core, such as metal, ceramic, or rigid polymer. In addition, risers may be adhered or attached in layers allowing selective removal of a portion of the thickness of a riser to accommodate incomplete tooth movement as the orthodontic treatment progresses.

In use, the dentist can prepare an impression of the teeth, with wax or by some other clinically acceptable means, and thus determine where the bite plate needs additional height to contact the teeth. A typical silicon boil and bite tooth guard would also be suitable for this purpose and is readily available. Based on the impression, the dentist can align the risers on the bite plate and affix them thereto. This process can then be repeated as needed during the tooth remodeling as the shape of the patient's dentition changes. Alternatively, where a wax impression is used, the dentist can align the wax impression with the bite plate, and push an X tack or other sharp instrument through the wax to mark the exact location where a riser is required. This process could be applied to any impressionable polymer that is sufficiently soft to easily penetrate, thus could be used with a boil and bite guard provided the guard has a combination of sufficient softness/and/or thinness to allow easy penetration. In yet another embodiment, the bite plate can be coated with a temporary dye of a different color than the bite plate so as to remove dye from the plate where contact is made, and the plate is then built up until each tooth is in contact with the riser. U-shaped wax or polymer thin strips can be available for the dental professional's use in this regard, wherein the strip is much thinner than the typical mouth guard.

In yet another embodiment, the risers and plate are accompanied by a sizing kit that includes a polymeric dip for coating the risers and plate combination. The dip is biocompatible, such as polyurethane or silicon, and provides a 0.5-5.0 mm, preferably 1-2 mm, coating on the bite plate/risers. Initially, the polymer is soft enough to allow the patient to bite into the polymer, thus perfecting the fit for each patients teeth, before completely hardening. This can be achieved with temperature (e.g., a boil and bite polymer), or with the use of post bite setting or crosslinking reagents, many of which are known in the art.

Risers are an elegant, low cost solution to the problem of making a standard bite plate that fits all patients, but there are patients whose teeth are so severely out of alignment, that a more complex solution is warranted. In such cases, a removable flexible pointer or wand can be affixed to the bite plate and the wand bent so that it contacts even the hardest to reach teeth. In this instance, a clamp is positioned on the bite plate with a slot for receiving a wand connector (or vice versa), which then holds the wand at variable points along its length, thus allowing the wand to be variable lengths.

The clamp can be slidably connected if desired, which allows accurate positioning of the clamp by the dental professional. Generally speaking, the clamp being somewhat bulky is placed at the front of the bite plate in a location as near the tooth to be contacted as possible without impinging on other soft tissues of the mouth and face. However, the wand having some possible length adjustments is still able to reach the recessed tooth. Further, since the wand is flexible, it can be continually repositioned to reach the tooth as remodeling occurs.

In some embodiments, the clamp and wand connector can be integral, but greater flexibility may be obtained with separate pieces, because the connector can be designed to rotate with respect to the clamp, thus allowing rotation of the wand as tooth position changes. The wand can also be integral to the connector, or both the connector and the clamp, but again greater flexibility is obtained if the wand is reversibly connected to the clamp via the connector because different length wands can be selected as appropriate for a particular patient. The wand could be constructed and fabricated in a variety of ways, but in one preferred embodiment, the wand is constructed of any flexible material, including metal or polymer, and the tip or entire wand can be coated with the same material coating the dental plate for patient comfort.

Another embodiment relies on the unique properties of some materials to be malleable under slow forces, but harden on a fast impact. For example, a shear-thickening fluid ("STF") is a non-Newtonian fluid whose viscosity increases with the rate of shear. In other words, it moves like a liquid until an object strikes or agitates it forcefully. Then, it hardens quickly. A simple and biocompatible example of an STF is a solution of nearly equal parts of cornstarch and water. If the solution is slowly stirred, it moves like a liquid. But when vibrated, its surface abruptly solidifies.

Such a non-Newtonian fluid can fill the space of a cavity or "cushion" on or within a leak proof layer within the bite plate, and will conform to recessed teeth when the patient bites on the fluid filled cushion slowly, but still transmit sufficient vibratory force when the device is activated due to the unique properties of the STF. Cushions, chambers, or capsules can easily be formed in the polymeric coating or glued or otherwise bonded to a stiff inner core of the dental plate, and silicone is already commonly used for such purposes. Further, the chamber can be made of a different polymer and placed over or under the polymeric coating that otherwise coats the dental plate, as needed for flexibility, strength and biocompatibility purposes.

Other examples of STF's are available. The fluid used in liquid body armor is made of silica particles suspended in polyethylene glycol (PEG). PEG may or may not be FDA acceptable, but the same effect is achievable using silica or steel beads and a biocompatible fluid, such as oil or syrup. Further, since the cushion is not intended to leak and can be designed to minimize or eliminate leakage, PEG may even be FDA acceptable in a well designed device. In use when the bite plate is bitten slowly, the cushion contents will conform to recessed teeth, but the beads (being rigid) will still transmit the vibratory force.

Additional non-Newtonian fluids are expected to become available with the advent of nanotechnology and the realization of additional applications of nanoparticles. For example, it is anticipated that buckminsterfullerenes or nanotubes mixed in oil or thick syrup will provide an FDA acceptable STF. These and other STFs are described in WO2007146703, EP1897609, US20080032899, and the like.

Another possible fluid applicable for use inside the cushion is magnetorheological (MR) fluid. MR fluids are oils that are filled with iron particles. Often, surfactants surround the particles to protect them and help keep them suspended within the fluid. The particles are tiny, measuring between 3 and 10 microns. However, they have a powerful effect on the fluid's consistency. When exposed to a magnetic field, the particles line up, thickening the fluid dramatically. The term "magnetorheological" comes from this effect. Thus, the vibrator can be combined with a magnetic field, thus stiffening the elastic bite plate covering material during use sufficiently to transmit vibration to the teeth.

In another use, the malleable bite plate covering combined with a sliding diaphragm that alters the fluid pressure of the covering's contents by forcing the contents of the cushion in front of the diaphragm, in a manner similar to a dam. The diaphragm can have protrusions that fit into detents on the stem or body of the bite plate (or vice versa) and the diaphragm can be moved along the bite plate at prescribed time intervals, thus changing the pressure that the cushion contents apply to the malleable bite plate covering. The change in this pressure allows the surface of the bite plate to maintain appropriate contact with the teeth allowing continuous application of the necessary and desired proximal vibratory forces.

Useful accessories for the vibrating dental device include travel or carrying cases and docking or charging stations. The travel case can be shaped similar to the vibrator and the dental plate, or can be box shaped with depressions inside that shape fit the unit or the pieces thereof. The travel case can also function as a charging station, and be equipped with a plug for connection to a standard wall socket. In addition, a base station that the vibrator fits into or "docks" with during recharging can be useful for home use. In some embodiments, the travel case is perforated so as to allow air circulation around the dental plate, thus providing good ventilation for air drying after use. In preferred embodiments, both the charging station and the vibrator are equipped with LED charge indicator lights.

The invention can also be improved by decreasing the size of the motor. A large number of very small vibrating motors are available, as shown in the table below. Many of the small vibrators currently used in cell phones and pagers are small motors with an offset weight that causes the motor to vibrate as the shaft turns and the weight pulls the motor from one side to the other. However, newer piezoelectric motors are being developed that would be preferred for use in the invention since they are even smaller and there are no moving parts.

| Company | Catalog | Size | Specifications |
|---|---|---|---|
| SURPLUS TRADERS ™ | MF820 | 8 × 4 mm (0.315 × 0.1575 inches) | 1.5 to 4.5 VDC weighted shaft |
| SURPLUS TRADERS ™ | MF918 | 0.45 × 0.16 inches | 1 VDC to 5 VDC 18 ohms Weighted shaft |
| MOTOROLA ™ | G13566 | 0.44 × 0.18 inches | 1 VDC to 9 VDC 10 ohms Weighted shaft |
| SURPLUS TRADERS ™ | MF835 | 0.45 × 0.24 inches | 1.3 Vdc 100 mA Weighted shaft |
| ELLIPTEC AG ™ | NA See U.S. Pat. No. 6,870,304 | 10 × 3 × 2 mm | 3-6 volts piezoelectric motor |
| MATSUSHITA ™ | V0296A | 0.24 inch diameter | 1.5 VDC Weighted shaft |
| SURPLUS TRADERS ™ | ME235 | 0.24 × 0.5 inches | 1.5 to 3 VDC 62 mA weighted shaft |
| PRECISION MICRODRIVES ™ | 304-002 | 4 m × 8 mm | 2.3 VDC to 3.6 VDC 100-120 mA 11000 rpm Weighted shaft |

In addition to electromagnetic motors and piezoelectric motors, other motor types can be used including mechanical actuators, ultrasonic motors and the like. Vibrations may be oscillating, random, directional, circular, and the like. Vibrators are well within the skill of the art, and several are described in the patent literature (and commercially available as seen above). For example, US20070299372, US20070255188, US20070208284, US20070179414, US20070161931, US20070161461, US20060287620, each incorporated by reference, describes various massagers (vibrators) and their motors.

Piezoelectric vibrator and piezoelectric motors can be generated using a variety of compositions and electrical properties that convert electrical energy to mechanical motion.

In one embodiment piezoelectric crystals or ceramics can be generated in a variety of sizes and shapes that will alter the frequency of vibration and voltage required. Piezoelectric materials include quartz, mica, calcite, apatite, topaz, berlinite ($AlPO_4$), tourmaline, Rochelle salt, barium titanate (Ba-$TiO_3$), lead titanate ($PbTiO_3$), lead zirconate titanate (Pb[$Zr_xTi_{1-x}$]$O_3$ or PZT), potassium niobate ($KNbO_3$), lithium niobate ($LiNbO_3$), lithium tantalate ($LiTaO_3$), sodium tungstate ($Na_xWO_3$), $Ba_2NaNb_5O_5$, $Pb_2KNb_5O_{15}$, and piezoelectric polymers like polyvinylidene fluoride (PVDF). Commercially available piezoelectric vibrators can be obtained from a variety of custom manufacturers' including TRS Technologies™, Inc. (State College, Pa.) and Omega Piezo™ (State College, Pa.), as well as a multitude of electronic suppliers including Electronic Supply Company™, Inc. (Kansas City, Mo.), All Electronics Co.™ (Van Nuys, Calif.), Radio Shack™ and the like.

Generally speaking, the vibrators are placed extraorally, thus allowing the use of a standard vibrator and disposable bite plates in a few basic sizes. However, motors can also be applied inside a bite plate at one or more desired locations so that it is adjacent to a tooth while in use (e.g. along the occlusal edge of the bite plate). The tiniest motors can be position inside the U of the bite plate and combined with wireless drives, as described below, for the minimum footprint and maximal patient compliance.

The dental plate itself generally contains a stiff core, such as metal, that is covered with a liquid-tight, elastic polymeric material to protect the user's teeth from the metal and to provide a biocompatible and pleasant mouth feel. Other stiff core material can also be employed including ceramic, polymers and resins. However, aluminum and steel are preferred as easy to work with, inexpensive and having some flex.

The dental plate may be coated with a polymeric coating, such as silicone rubber, polyethylene (PE), high density PE (HDPE), polycarbonate, polyurethane, polypropylene (PP), polyvinylchloride (PVC), polymethyl methacrylate, polyvinylidene fluoride, polyesters, acrylics, vinyl, nylon, rubber, latex, Teflon, or similar material. Further, the coating need not cover the entire dental plate, but only the oral portions thereof. Preferably, the polymer will not have an objectionable taste and will be FDA approved, such as silicone rubber, polypropylene, HDPE, and the like. The dental plate can also comprise two plastics, an inner layer for strength and structural integrity, and a more pleasing outer coating for patient compliance.

In another embodiment the bite plate coating and other parts of the appliance that contact oral tissues have a selection of flavorings for additional comfort in use of the appliance.

Depending on which teeth or regions of dentition that need to be treated, different dental plate shapes are possible. However, generally, the dental plate is flat to allow contact of the occlusal surfaces of all teeth when the dentition has reached a final level plane and U-shaped. Alternatively, the dental plate may cover only a portion of the dentition, thus being restricted to fewer teeth in use and differential tooth movement as a planned treatment approach. The dental plate can also have one or more perpendicular edges or phalanges, said edges being positioned to contact the facial and lingual surfaces of the teeth and possibly even apically beyond the gum line. In preferred embodiments, the dental plate has a U-shaped bite plate and a prong for attachment to the vibrator, thus in general being Y shaped.

The device can be programmable and have memory capacity, as described in co-pending application Ser. Nos. 11/773,849 and 11/773,858, incorporated herein by reference. Thus, the frequency, amplitude and duration can be modified as needed, and the usage of the device monitored for compliance by the dentist or patient. In addition, the device can alter the application of the force in frequency, duration and amplitude regionally as prescribed for differential tooth movement throughout the dentition.

Communication with other processors can be direct or wireless. The electronics can be contained within the same housing as the vibrator, or can be in a separate unit connected to the vibrator with a wire and port. In preferred embodiments, the communication is wireless via a near radio frequency source.

In one embodiment, the interior of the bite plate contains a switch that is activated when sufficient pressure is applied to the bite plate. Thus, no additional on/off switch is needed and the vibrator automatically engages when the bite plate is bitten.

In another embodiment, the processor can send and/or receive information from a remote processor. The processor communicates with a remote computer via internet, phone, wireless, infrared, satellite, cellular, cable, modem, or other form of electronic communication. The processor can run software that captures usage frequency and duration. In yet another aspect, a method for recording compliant use of an orthodontic device, where the device has electronic media that captures information about usage, tooth position, and/or device function for download and analysis.

Batteries, either non-rechargeable or rechargeable, or other electric source can drive the vibrational source. If a rechargeable battery is used it can be charged from any type of power source including USB ports, RS-232 ports, FireWire ports, transformer, or unique docking power source, for example. Coin batteries are preferred in some embodiments, and in preferred embodiment there is both a small coin battery and a rechargeable battery for maximum flexibility.

The device can be used alone, or in combination with other orthodontic devices. In some embodiments, the appliance can be used to speed boney remodeling in orthodontic uses with traditional orthodontic fixed appliances or aligner based treatments or any other appliance used for tooth movement. In other embodiments the appliance can be used to enhance boney remodeling in periodontal and oral surgical uses.

The device of the invention can be used in a variety of oral and maxillofacial applications including malocclusion, trauma repair, temporomandibular joint and muscle disorders (TMJDs), Lefort and other skeletal facial fractures, craniofacial anomalies such as boney clefts, bone defects, dentofacial deformities, dental implants, periodontal bone grafts as well as tooth, muscle, nerve, tendon, ligament, bone, and connective tissue repair.

Thus, the invention also includes a method for movement of an individual tooth or groups of teeth by applying differential vibration to selected areas of a bite plate at frequencies between 0.1 to 400 Hz (or 5-50 or 10-30 Hz) and a force of 0.01-2 Newtons (or 0.1-1 or 0.2-0.6 Newtons) for a period of 1-60 minutes, preferably about 1-30 or 1-10 minutes. This is followed by a period of recovery, ranging from 2-24 hours, preferably from 4-12 hours, and the cycle is repeated until one or more teeth are successfully moved. More particularly, the orthodontic appliance of the invention has a vibrational source capable of providing a vibratory force at a frequency of between 0.1 to 400 Hz and a force of 0.01-2 Newtons.

DESCRIPTION OF EMBODIMENTS OF THE INVENTION

The following examples are illustrative only.

Example 1

Figure 1:
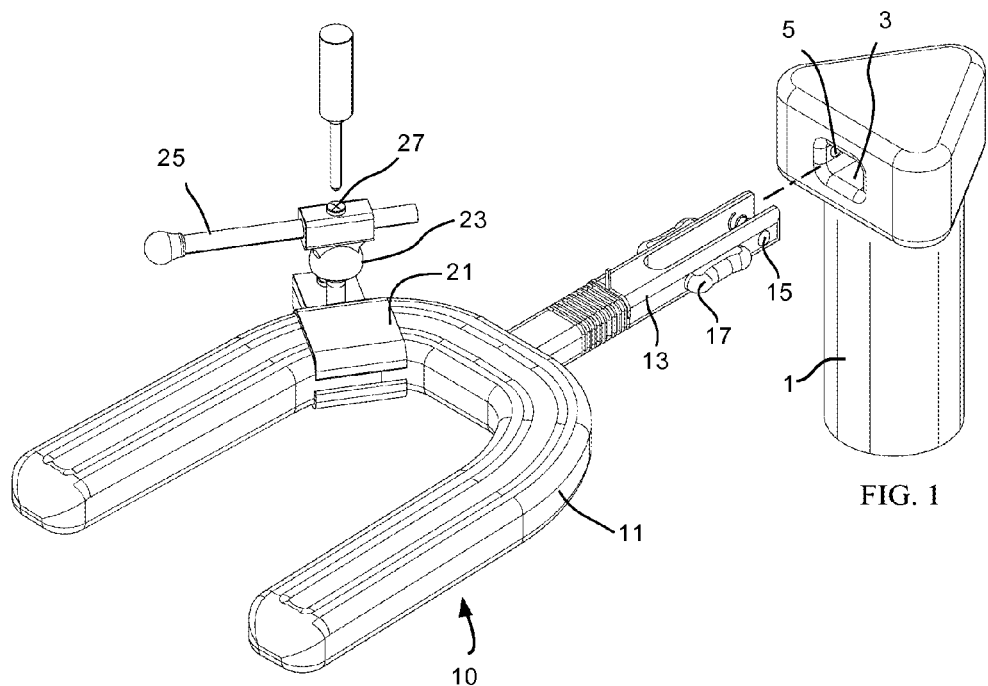
FIG. 1 shows the disposable dental plate 10, with bite plate 11, prong 13 and corresponding socket 3 on a extraoral vibrator 1. It also illustrates clamp 21, connector 23 and wand 25 system used to reach severely misaligned teeth, wherein the clamp is attached to the bite plate 11 in this embodiment.
Figure 2A:
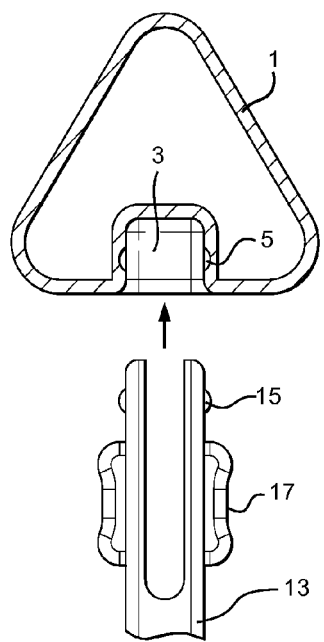
FIGS. 2A, B, C and 3A, B, C shows various prong 13 and socket 3 configurations, with protrusions 15 snap fitting into depressions 5.
Figure 2B:
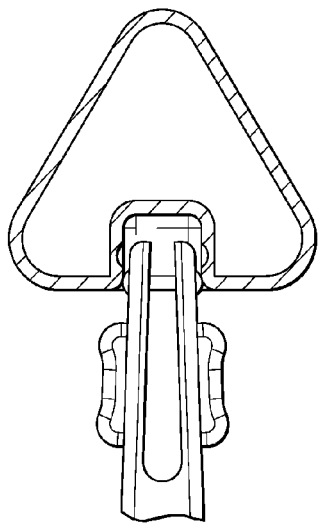
Figure 2C:
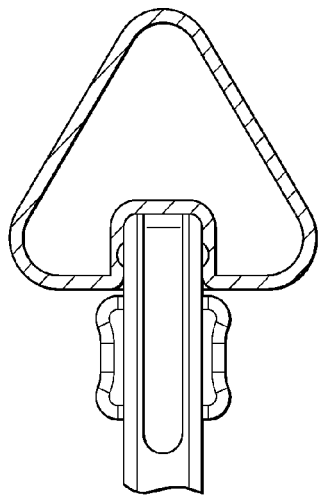
Figure 3A:
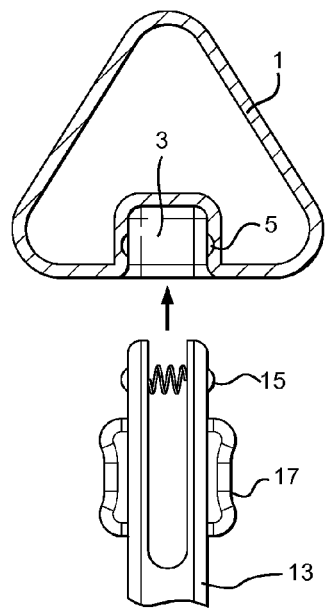
Figure 3B:
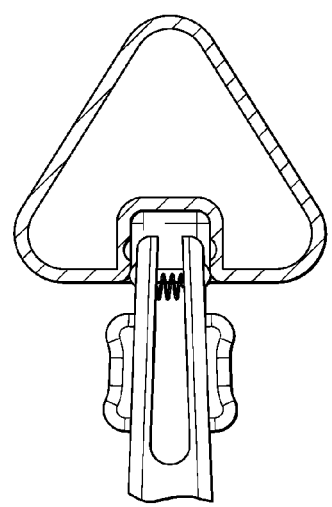
Figure 3C:
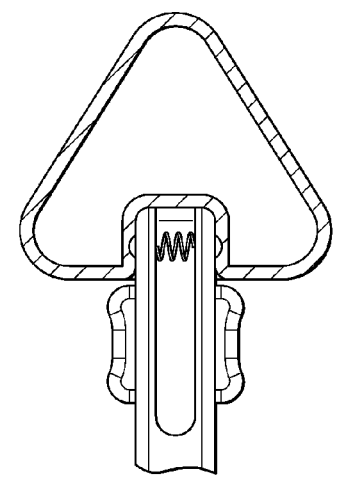

The device of FIGS. 1-3 illustrates a snap fit between the prong 13 of the dental plate 10 and the socket 3 of the vibrator 1. In the embodiments shown, the prong has protrusions 15 that fit into recessions 5 inside the socket 3. Button 17 can be used to release the protrusion from the recessions when the dental plate is removed. Various means of biasing the protrusions outward so as to lock into the socket are available, including coil, leaf or torsion springs, and the like. Alternatively, if the prong is bifurcated or is otherwise compressible the material itself may provide the biasing means. We have illustrated a rectangular prong and socket, but other shapes are possible requiring only that the socket accommodate the prong in a snap or locking fit. Further, we have illustrated the prong having the protrusions and release button, but the reverse is also possible and the protrusions can be contained in the socket of the vibrator.

Example 2

Figure 4:
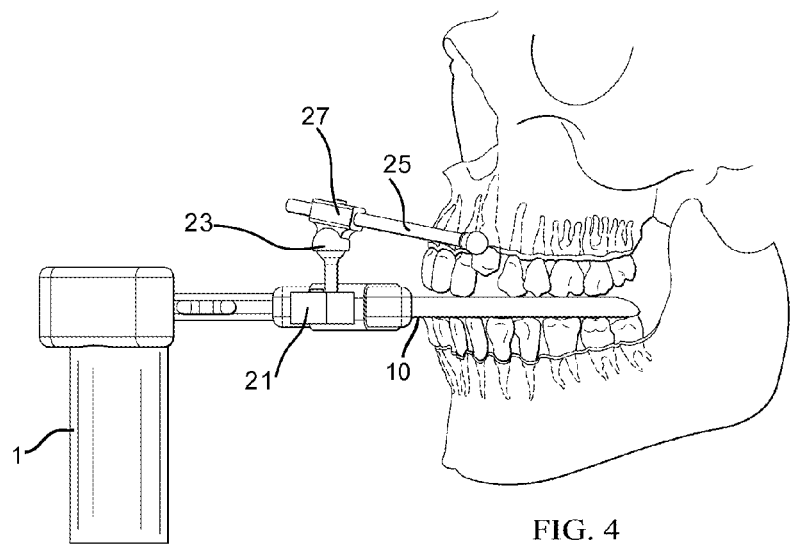
FIG. 4 shows another perspective of the clamp 21, connector 23, wand 25 systems used to reach severely misaligned teeth. Here the clamp 21 is attached to the prong of the dental plate, and the wand is flexed as needed to reach a recessed tooth.

FIGS. 1 and 4 illustrate the wand system designed to reach severely misaligned teeth. In this embodiment, wand 25 is made of a flexible material, such as metal, and can be completely or partially coated with a polymeric material such as silicone. The wand 25 is removably attached to the dental plate 10 on either the bite plate 11 or the prong 13 via clamp 21 and optionally a connector 23 that functions to reversibly and optionally rotationally couple the clamp and the wand. In use, the wand is flexed to meet the recessed or misaligned teeth and the clamp 21 can be positioned as needed on the bite plate or the prong. In one embodiment, a tightening or locking means 27 is used to tighten, fix or lock the connector into position so that the wand sits in a particular orientation. In preferred embodiments, the clamp is attached to the prong, thus remaining outside the mouth during use.

Example 3

Figure 5A:
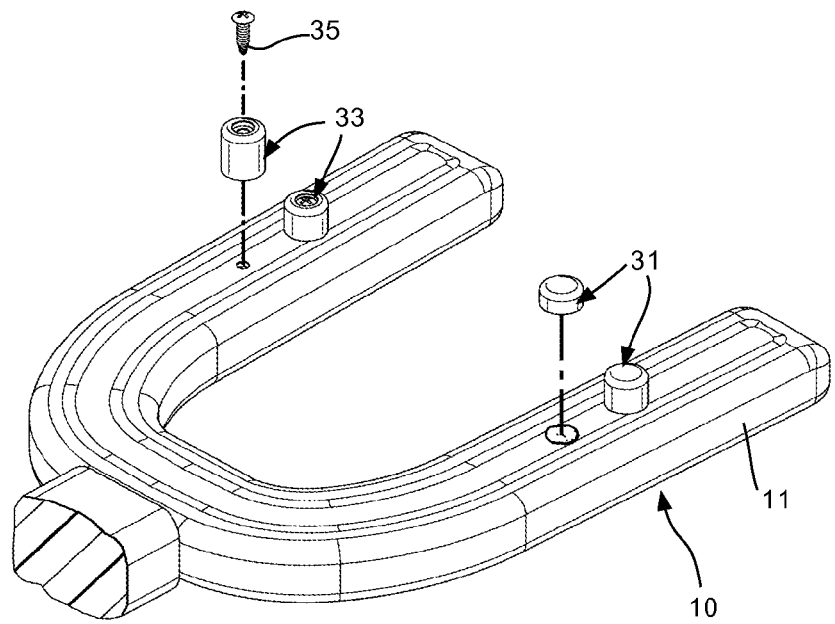
FIGS. 5A and B show top and side views of a dental plate 10 wherein risers 31 or 33 are used to build up the bite plate to reach recessed teeth. A screw 35 is shown attaching riser 5 to the dental plate, but riser 31 can be glued or otherwise bonded to the dental plate.
Figure 5B:
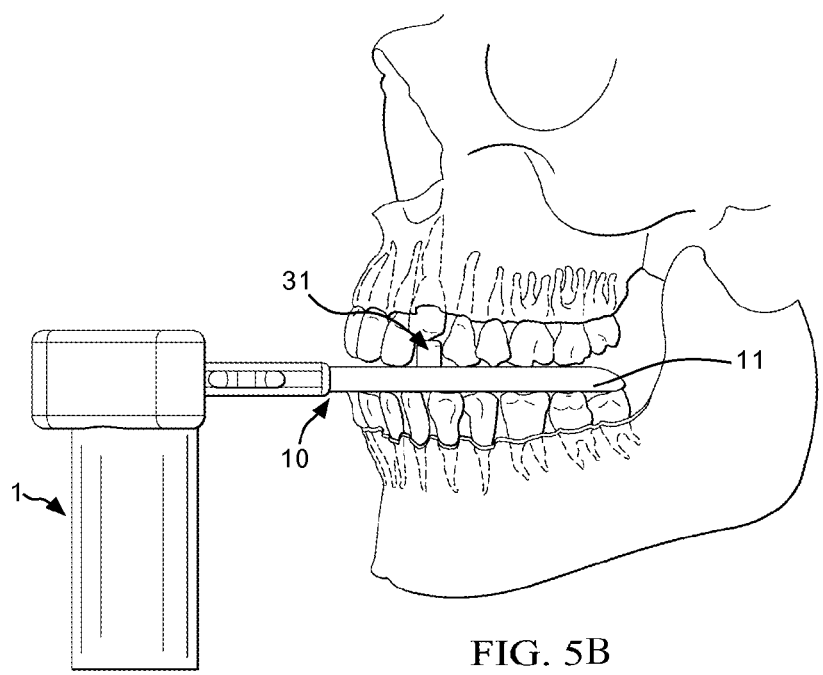

The device of FIGS. 5A and 5B show a much simpler means of reaching recessed teeth, comprising adding risers 31 to the bite plate 11 at appropriate locations. The risers 31 can be glued, heat welded, welded or otherwise bonded to the bite plate, or can be attached by an attaching means, such as a screw 35, rivet, bolt, nail, staple, pins, and the like. Shown is a separate screw 35 that passes through the riser and threadably connects to the bite plate. Risers that are bonded to the bite plate are preferred since this provides the maximum flexibility in placement of the riser. We have illustrated risers for individual teeth, but risers can also be elongated to contact multiple teeth, as needed for a particular dentition.

Example 4

Figure 6A:
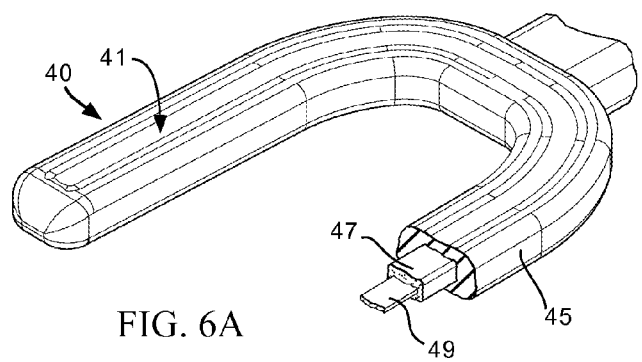
FIGS. 6A and 6B show a fluid filled dental plate 40 having an optional stiff inner core 49, surrounded by a fluid 47 that is encapsulated within a polymeric coating or cover 45. When the patient bites the plate, the fluid will conform to uneven dentition. An optional diaphragm 43 is included (here on the prong) and serves to force fluid forward so as to reach severely recessed teeth.
Figure 6B:
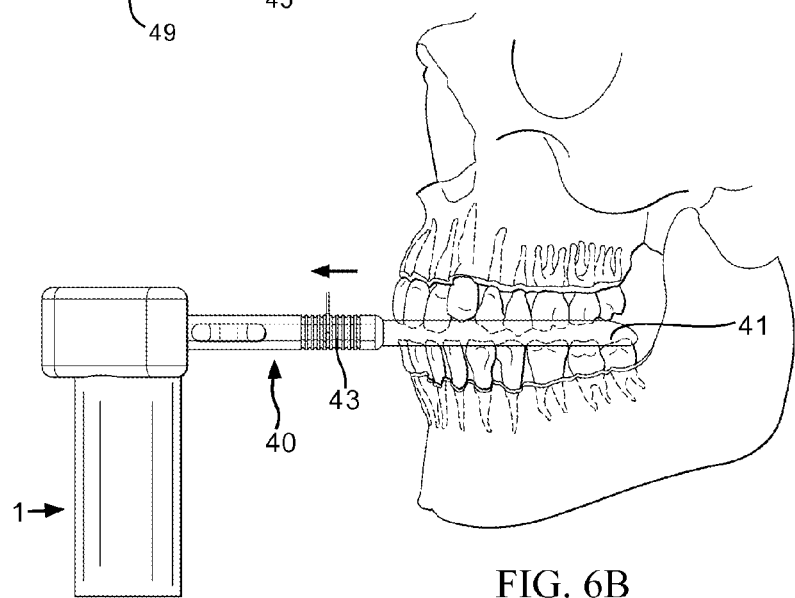

The device of FIGS. 6A and 6B illustrates a dental plate 40 having a bite plate portion 41 comprising an inner core 49, preferable of metal, ceramic, or stiff resin or polymer. The bite plate and inner core are encased in a polymeric capsule (aka pillow or chamber) 45 which serves to contain fluid 47, preferable a shear stiffening fluid (STF) or a magnetorheological (MR) fluid that will serve to conform to the teeth when slowly bit by the patient, but will stiffen when force or a magnetic field is applied, allowing the fluid to transmit the vibrational force to the teeth. The dental plate can also be combined with an optional diaphragm 43 that serves to force fluid further forward into the bite plate portion, thus causing the pillow or capsule to expand and reach even the most recessed teeth.

Figure 6C:
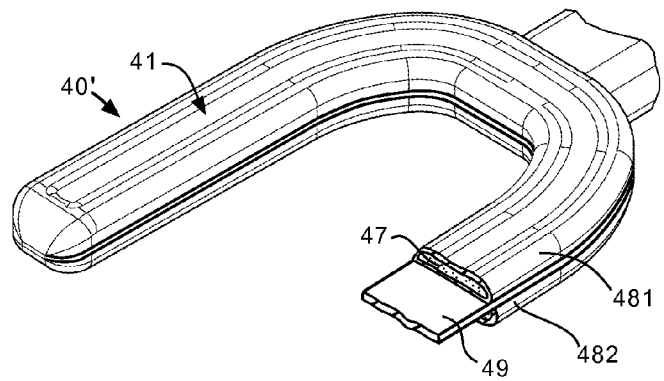
FIG. 6C shows the dental plate 40' similar to that in FIG. 6A, with upper and lower capsules 481, 482 attached to the stiff inner core 49.

We have illustrated a capsule that completely surrounds the bite plate, but upper and lower capsules 481, 482 or both are also possible, as shown in FIG. 6C, and may be preferred as a means of conserving the amount of STF fluid. Further, the capsules may be fabricated independently, and bonded to a standard bite plate as needed for particular patients use. Although we have illustrated a long capsule covering the entire oral portion of the bite plate, it can also be shorter and contact fewer teeth, or even a single tooth, in a manner similar to the risers.

Example 5

Figure 7A:
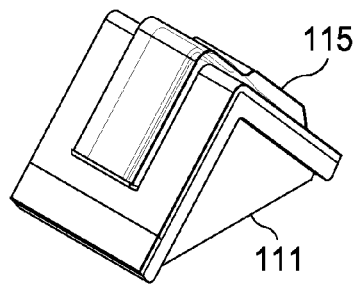
FIG. 7A-N shows various accessories for the vibrating dental device of the invention.
Figure 7B:
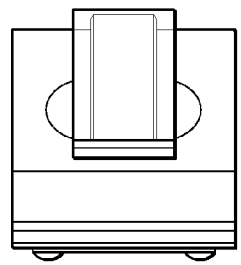
Figure 7C:
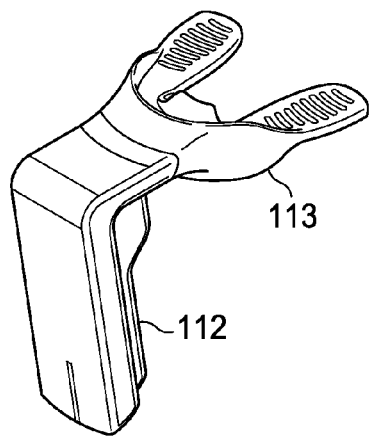
Figure 7D:
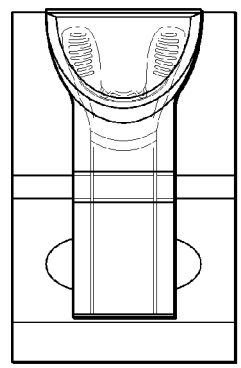
Figure 7E:
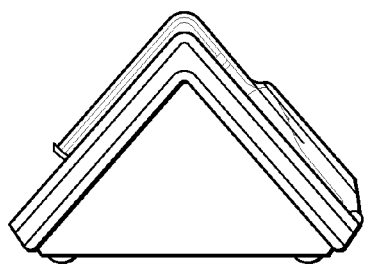
Figure 7F:
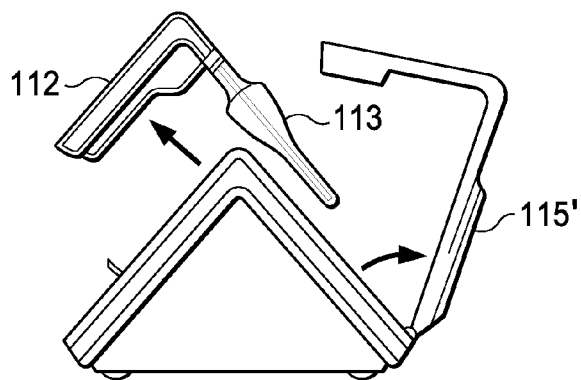
Figure 7G:
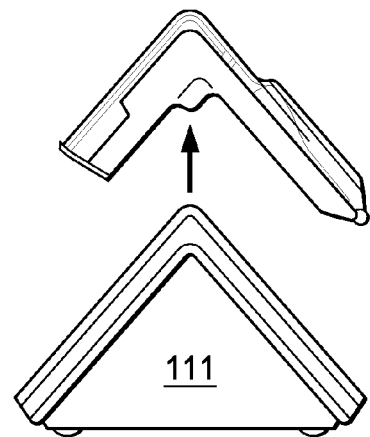
Figure 7H:
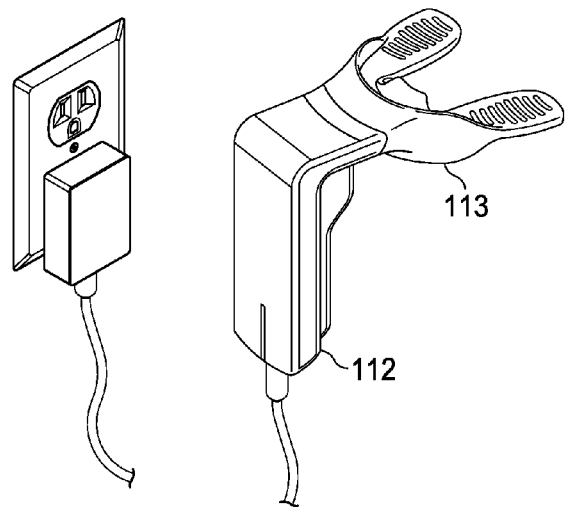
Figure 7I:
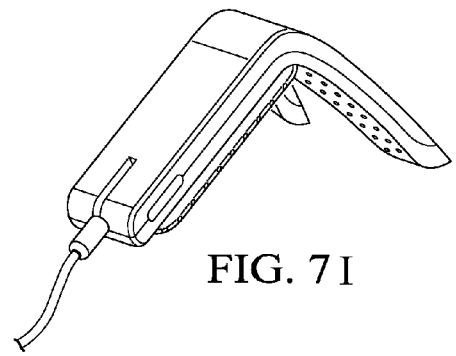
Figure 7J:
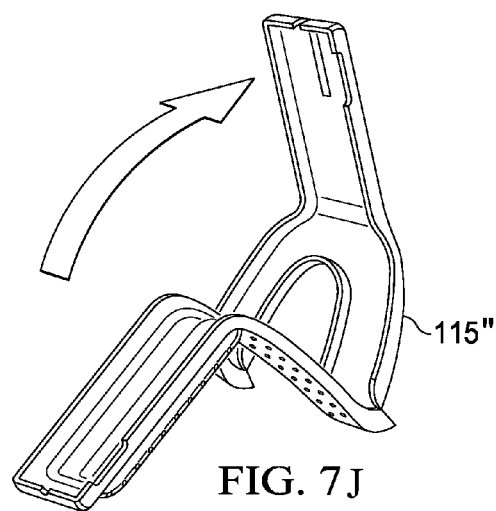
Figure 7K:
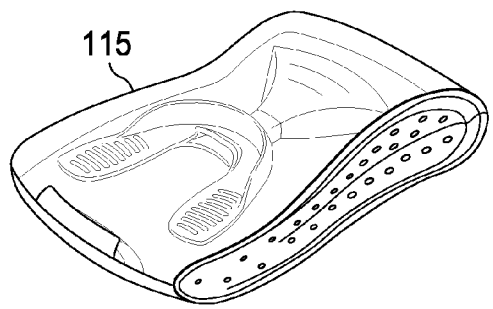
Figure 7L:
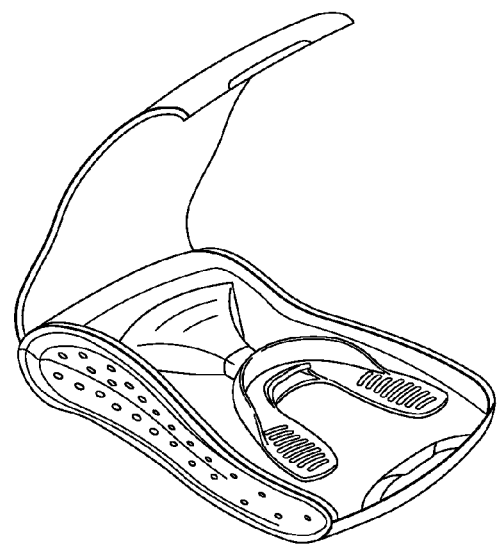
Figure 7M:
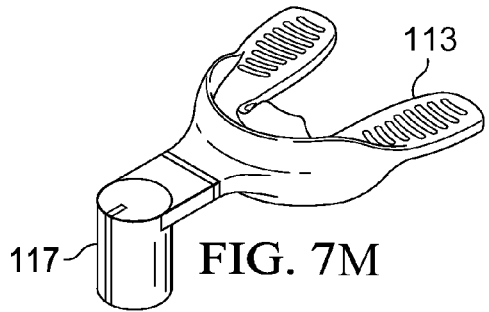
Figure 7N:
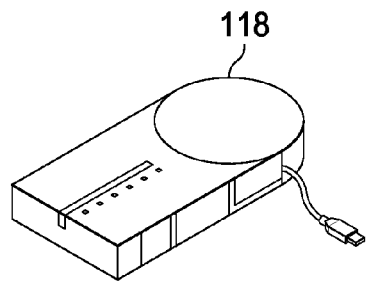
Figure 8A:
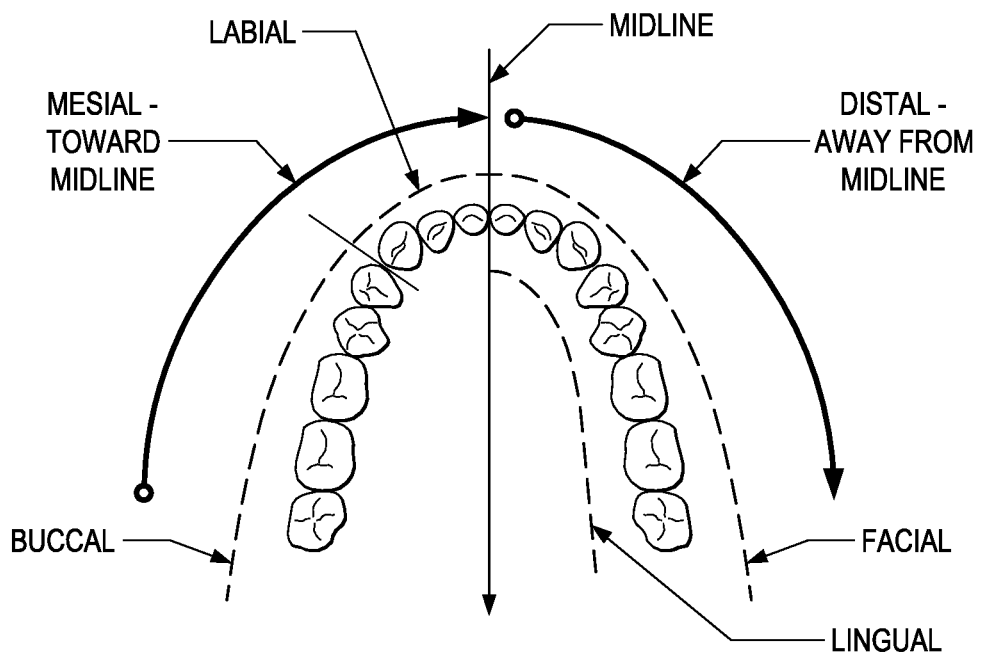
FIGS. 8A-B provide dental nomenclature.
Figure 8B:
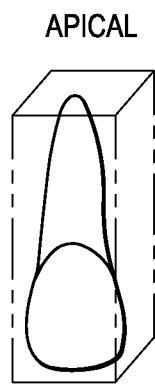

The device of FIG. 7A-N illustrates various vibrating dental device accessories. There is shown perspective (FIG. 7A), top (FIG. 7D) and side views (FIGS. 7B, 7E) of a combination base 111 and carrying case 115 embodiment, wherein the base 111 is a charging station (cord not shown) having LED charge indicator lights, and the case 115 snap fits into the base unit for charging, but can be removed for transport, as shown in FIGS. 7F and 7G. The device also has LED charge indicator lights. Dental plate 113 connected to extraoral vibrator 112 is also shown in FIG. 7C.

FIG. 7H to 7J show a unitary case 115' and charging unit combination (cord shown), again having LED lights. This embodiment shows a latch or button release for opening the case, and a portion of the case is perforated for air circulation. The cord in 7H can be removably attached to the carrying case, or can be plugged directly into the unit through a small hole in the carrying case. Alternatively, the cord can be permanently or reversibly mounted to the case and the case comprises operable connections for charge transfer to the vibrator's rechargeable battery.

FIGS. 7K and 7L show a simple carrying case 115" that has a latch, smooth ergonomic shape and soft foam insert configured to fit the device. FIGS. 7M and 7N show yet another embodiment, wherein the charge unit 118 plugs directly into a socket on an extremely small vibrator 117 (socket not shown) via a retractable cord. An additional cord (not shown) connects the charger to a wall socket, or the device can plug directly into a socket (not shown).

The following references described herein are expressly incorporated in their entirety:
U.S. Pat. No. 4,883,046
U.S. Pat. No. 4,244,688, U.S. Pat. No. 4,348,177, U.S. Pat. No. 4,382,780
U.S. Pat. No. 5,030,098
U.S. Pat. No. 5,967,784
U.S. Pat. No. 6,632,088
U.S. Pat. No. 6,684,639, U.S. Pat. No. 6,832,912, U.S. Pat. No. 7,029,276
U.S. Pat. No. 7,163,399
U.S. Pat. No. 7,192,281
JP2007260158
Ser. Nos. 11/773,849, 11/773,858, 61/040,777
US20070299372, US20070255188, US20070208284, US20070179414, US20070161931, US20070161461, US20060287620
US20080227047, US20080227046, 61/040,777, 61/074,884
WO2007146703
EP1897609
US20080032899

What is claimed is:

1. A dental bite plate comprising:
   an inner stiff core;
   an upper capsule formed by a flexible polymeric material, wherein the upper capsule is attached to an upper surface of said inner stiff core; and
   a lower capsule formed by a flexible polymeric material, wherein said lower capsule is attached to a lower surface of the inner stiff core, wherein said upper capsule and said lower capsule are filled with a shear-thickening non-Newtonian fluid that is malleable when a slow force is applied thereto, but that stiffens when a vibratory force is applied thereto, wherein said inner stiff core is U-shaped; and wherein said upper capsule and said lower capsule are each U-shaped to contact a patient's entire dentition.

2. The dental bite plate of claim 1, wherein the shear-thickening non-Newtonian fluid is selected from the group consisting of a mixture of corn starch and water, a combination of rigid beads and oil or syrup, a combination of nanoparticles and oil, and a combination of nanoparticles and syrup.

3. The dental bite plate of claim 1, wherein the dental bite plate has a prong protruding from a labial midline of said dental bite plate for connecting to an extraoral vibrator.

* * * * *